United States Patent
Melkoniemi et al.

(10) Patent No.: US 10,342,495 B2
(45) Date of Patent: Jul. 9, 2019

(54) METHOD AND SYSTEM FOR PROVIDING AN EARLY RISK RECOGNITION MONITORING

(71) Applicant: NOKIA TECHNOLOGIES OY, Espoo (FI)

(72) Inventors: Sami Melkoniemi, Espoo (FI); Stefano Campadello, Espoo (FI); Niku Oksala, Tampere (FI)

(73) Assignee: Nokia Technologies Oy, Espoo (FI)

( * ) Notice: Subject to any disclaimer, the term of this patent is extended or adjusted under 35 U.S.C. 154(b) by 749 days.

(21) Appl. No.: 14/891,704

(22) PCT Filed: May 19, 2014

(86) PCT No.: PCT/FI2014/050376
§ 371 (c)(1),
(2) Date: Nov. 17, 2015

(87) PCT Pub. No.: WO2014/184448
PCT Pub. Date: Nov. 20, 2014

(65) Prior Publication Data
US 2016/0081628 A1    Mar. 24, 2016

(30) Foreign Application Priority Data
May 17, 2013  (FI) .................................... 20135530

(51) Int. Cl.
*A61B 5/1455*    (2006.01)
*A61B 5/00*    (2006.01)
(Continued)

(52) U.S. Cl.
CPC .......... *A61B 5/7275* (2013.01); *A61B 5/0008* (2013.01); *A61B 5/01* (2013.01);
(Continued)

(58) Field of Classification Search
None
See application file for complete search history.

(56) References Cited

U.S. PATENT DOCUMENTS

| | | |
|---|---|---|
| 5,050,612 A | 9/1991 | Matsumura |
| 6,010,455 A | 1/2000 | Barnett et al. |
| (Continued) | | |

OTHER PUBLICATIONS

Schey B.M., et al., Skin temperature and core-peripheral temperature gradient as markers of hemodynamic status in critically ill patients: A review. Heart & Lung, vol. 39, No. 1, pp. 27-40.
(Continued)

*Primary Examiner* — Eric F Winakur
*Assistant Examiner* — Marjan Fardanesh
(74) *Attorney, Agent, or Firm* — Locke Lord LLP

(57) ABSTRACT

A system for providing an early risk recognition monitoring by measurement of a peripheral tissue perfusion of a patient instead of clinically significant changes in systemic blood pressure and/or blood flow comprises a wristband device for gathering measurement data of the patient. The device measures a first temperature ($t_1$) of the patient at the first wrist (or distal antebrachium) point and a second temperature ($t_2$) of the patient at the second finger point, whereupon the system determines altered peripheral tissue perfusion by determining temperature gradient (Δt) between said first and second points. If the gradient (Δt) exceeds or deceeds a predetermined range, the system construes the exceeding as a peripheral vasoconstriction and the deceeding as a peripheral vasodilatation, and thereby provides a first early risk recognition phase (p1) and transmits it as a warning indication to end devices of health care personnel.

18 Claims, 2 Drawing Sheets

(51) Int. Cl.
*A61B 5/01* (2006.01)
*A61B 5/026* (2006.01)
*A61B 5/0205* (2006.01)
*A61B 5/11* (2006.01)
*A61B 5/021* (2006.01)
*A61B 5/08* (2006.01)
*G16H 50/30* (2018.01)

(52) U.S. Cl.
CPC ............ *A61B 5/015* (2013.01); *A61B 5/026* (2013.01); *A61B 5/02055* (2013.01); *A61B 5/0261* (2013.01); *A61B 5/6824* (2013.01); *A61B 5/6826* (2013.01); *A61B 5/6831* (2013.01); *A61B 5/7285* (2013.01); *A61B 5/021* (2013.01); *A61B 5/0816* (2013.01); *A61B 5/11* (2013.01); *A61B 5/14552* (2013.01); *A61B 5/7278* (2013.01); *A61B 2560/0252* (2013.01); *A61B 2562/0219* (2013.01); *A61B 2562/0223* (2013.01); *G16H 50/30* (2018.01)

(56) References Cited

U.S. PATENT DOCUMENTS

| | | |
|---|---|---|
| 2003/0107487 A1 | 6/2003 | Korman et al. |
| 2007/0225614 A1 | 9/2007 | Naghavi et al. |
| 2008/0001735 A1 | 1/2008 | Tran |
| 2008/0027330 A1 | 1/2008 | Naghavi et al. |
| 2008/0081963 A1 | 4/2008 | Naghavi et al. |
| 2010/0081941 A1 | 4/2010 | Naghavi et al. |
| 2010/0081942 A1 | 4/2010 | Huiku |
| 2010/0100004 A1 | 4/2010 | Van Someren |
| 2011/0077474 A1 | 3/2011 | Huiku |
| 2012/0083672 A1 | 4/2012 | Zhiqiang et al. |
| 2012/0101350 A1 | 4/2012 | Bychkov |
| 2012/0271121 A1 | 10/2012 | Della Torre et al. |

OTHER PUBLICATIONS

International Search Report and Written Opinion dated Sep. 16, 2014 in PCT/FI2014/050376, 14pp.
Lima, A. & Bakker, J., "Noninvasive monitoring of peripheral perfusion", Intensive Care Medicine, vol. 31, No. 10, Oct. 2005, p. 1316-1326.
Talke, P. & Stapelfeldt, C., "Effect of peripheral vasoconstriction on pulse oximetry", Journal of Clinical Monitoring and Computing, vol. 20, No. 5, Oct. 2006, pp. 305-309.
"Pulse Oximetry", Wikipedia article (online), Apr. 23, 2013, <URL: http://en.wikipedia.org/w/index/php?title=Pulse_oximetry&oldid=551862466>section 'Limitations', 6 pages.
Finnish Patent and Registration Office Opinion on Patentability dated Feb. 26, 2014 for Application Serial No. 20135530, 8 pp.

METHOD AND SYSTEM FOR PROVIDING AN EARLY RISK RECOGNITION MONITORING

TECHNICAL FIELD OF THE INVENTION

The invention relates to a method and system for providing an early risk recognition monitoring, as well as to a wristband device and a computer program product.

BACKGROUND OF THE INVENTION

In particular patients with acute illness that have been admitted to hospital, patients that have been operated on (major surgery in particular), elderly patients and patients with multiple pre-existing diseases have high risk to have Serious Adverse Events (SAE) such as hospital infections, respiratory function disturbance, circulatory disturbance and ultimately cardiac arrest during their hospital stay. For example the prevalence for the risk of imminent cardiac arrest is approximately 5% in hospitalized bedbound patients admitted to acute care departments. Patients that have been discharged from intensive care units (ICUs) without treatment limitations have also an increased risk of SAE resulting in medical emergency team review, readmission to ICU or even death. In spite of the initial recovery from the critical illness, nearly 10% of discharged ICU patients die on general wards and approximately 7 to 10% are acutely readmitted to ICU. Currently the observation and reaction to vital function disturbances rely on high cost human resource available in regular wards. Today there are increasing attempts to optimize production, effectiveness and efficacy in the health care. Attempts to reduce costs and increase the production rely by and large on reducing the number of staff in the wards. At the same time population ages and patients have at the time of hospital admission higher number of chronic pre-existing illnesses. The afore mentioned scenario with the attempts to increase production evolves to untoward risk field with unacceptably high rate of in-hospital cardiac arrests in worst case and prolonged hospitalization with long lasting human suffering and further costs to the society and individuals and families.

There are multiple risk factors which are associated with increased morbidity and mortality among hospitalized patients in general and in post-ICU patients in particular. These factors are related to hospital/ICU admission type, patient characteristics and several variables related to the disease, the patient and the treatment. At the same time, recent studies regarding medical emergency teams (MET) and prevalence of MET activation criteria in general wards imply that the ward level care in hospitals is often suboptimal. Basic vital functions (or dysfunctions) are not recorded or treated as would be expected. If this is applied to post-ICU patients too, recovery from critical illness may be compromised even after successful intensive care and discharge from ICU.

Results from previous studies show that prevalence of abnormal vital signs, recognized as positive MET criteria, was worryingly high among patients discharged from intensive care. Altered vitals were not regarded as early signs of deterioration requiring intervention, when presented to ward staff, even though MET has been active in hospital since 2009. After the first 24 h in general ward, recorded vital deviations (measured heart rate, systolic blood pressure, peripheral arteriolar oxygen saturation and respiratory rate) and attending nurse's concern about patient were the only factors independently associated with SAEs among discharged ICU patients. As a conclusion, simple vital function measurement and attending ward nurse's subjective assessment facilitate early detection of post-ICU patients at risk.

For early risk recognition few vital biosignals are typically monitored, such as blood pressure, heart rate, blood oxygen saturation and respiratory rate. According to conventional case the blood pressure is measured by a pressure cuff, which heavily interferes with or even blocks the blood circulation. Thus it interferes e.g. with other measurements, such as measurement of blood oxygen saturation at fingertip. In addition many of the known systems have plurality of sensors with lots of wires located around the body of the patient, which makes the systems inconvenient, as well as also unhygienic.

SUMMARY OF THE INVENTION

An object of the invention is to alleviate and eliminate the problems relating to the known prior art. Especially the object of the invention is to provide a system for providing an early risk recognition monitoring so that the measurement of different biosignals does not interfere with each other or any other measurement, such as that no blood circulation is blocked or interfered or the mobility of the user is not limited. In addition the object is to provide an easy, hygienic and mobile, as well as an accurate, fast, energy-efficient and reliable system.

The object of the invention can be achieved by the features of independent claims.

According to an embodiment of the invention an early risk recognition monitoring is provided by measurement of the adequacy or lack thereof of a peripheral tissue perfusion of a patient as a surrogate for and/or instead of clinically significant changes in systemic blood pressure and/or blood flow. An altered peripheral tissue perfusion is caused or due to either peripheral vasoconstriction or vasodilatation or altered blood flow or combination thereof. According to the invention the possibly altered peripheral tissue perfusion is determined by determining a skin temperature gradient ($\Delta t$) between two points, which is changed due to either peripheral vasoconstriction or vasodilatation or altered blood flow or combination thereof.

The measurement according to the invention is advantageously continuous and non-interfering measurement, which means that the measurement of the peripheral tissue perfusion is performed without interfering, such as manipulating or obscuring the blood circulation of the patient. This is possible due to the temperature measurements and because there is no need for measuring blood pressure using a typical pressure cuff or any other devices interfering, limiting or even blocking the blood circulation. This is possible according to the invention because the peripheral tissue perfusion is determined by measuring temperature gradient ($\Delta t$) and because the temperature needed are measured with infrared temperature sensors. In particular advantages are achieved by using IR sensors, because they do not need any especially tight physical contact with the body, whereupon they do not interfere with the blood circulation. In addition the IR sensors do not essentially have any thermal capacitance in view of measurement, whereupon the measurement do not essentially influence the value of temperature to be measured and additionally IR measurement is very fast for example when compared to measurements done needing thermal conduction, such as thermistors.

In the monitoring according to embodiment of the invention a first temperature ($t_1$) of the patient is measured at the first wrist point (or distal antebrachium), as well as a second temperature ($t_2$) of the patient is measured at the second finger point. The first wrist point is advantageously a distal antebrachium, and the second finger point is a location at the root end of finger, proximal to the proximal interphalangeal joint but distal to the metacarpophalangeal joint. The temperatures ($t_1$) and ($t_2$) are measured with suitable temperature sensors, such as infrared sensors, as an example. According to an example the temperature sensors are in a wristband like device, which is configured to gathering measurement data of the patient for the monitoring.

If the determined temperature gradient ($\Delta t$) exceeds a predetermined range, such as e.g. 1-4° C., or advantageously 2-3° C. [e.g. 1-4° C., most preferably 2-3° C.], a first early risk recognition phase ($p_1$) is provided. In the first early risk recognition phase an ($\Delta t$) exceeding of the upper limit of the range is construed as the peripheral vasoconstriction and an ($\Delta t$) deceeding of the lower limit of the range is construed as the peripheral vasodilatation, correspondingly.

In the method the temperature gradient is advantageously calculated between the measurement points 1 and 2. A normal temperature gradient for healthy people in a rest is 1-4° C. If the gradient exceeds 4 degrees, this implicates peripheral vasoconstriction and reduced perfusion and microcirculation which can be due to rapid decrease in systemic blood pressure (common causes of this are hemorrhagia, cardiogenic shock, cold phase of septic shock, peripheral arterial occlusion). It can also be caused by disturbances in autonomous nervous regulation as occurs in Raynaud's phenomenon and by action of anesthetic agents. Peripheral vasoconstriction is basically a protective mechanism which is utilized to maintain sufficient blood pressure for the vital organs such as brain and heart. For example, clinically significant hemorrhagia results in rapid loss of circulating blood volume and decrease in systemic blood pressure if increased heart rate and vascular constriction cannot overcome the loss of volume. Cardiogenic shock (common causes of which are myocardial injury due to ischemia or infection, conduction defects due to various causes and valvular dysfunction) results in rapid decrease in cardiac output resulting in subsequent decrease in systemic blood pressure. In the cold phase of septic shock, the failing heart and decreased intravascular fluid volume result in decreased blood pressure. Peripheral arterial occlusion results in rapid decrease in arterial pressure.

In addition another phase, such as more detailed, versatile or accurately analysed early risk recognition phases may also be performed according to embodiments of the invention described in more detailed manner elsewhere in this document.

According to an embodiment also a third ambient temperature ($t_3$) is determined for example in the case of the ($\Delta t$) exceeding, and if the third ambient temperature ($t_3$) is within a predetermined range (signal for peripheral vasoconstriction is not due to low or vasodilatation due to high ambient temperature), a second early risk recognition phase ($p_2$) is provided. Other causes such as low ambient temperature, which results in vasoconstriction and autoregulation of arteriovenous shunts by means of heat conservation are detected by ambient temperature sensor and utilized in the analysis.

Also absolute temperatures ($t_1$) and ($t_2$) can be determined in the case where the gradient ($\Delta t$) is below a predetermined threshold [like essentially 0° C.] and if the absolute temperatures ($t_1$) and ($t_2$) are within a predetermined range [like essentially 35° C.-37° C.], the case is construed as peripheral vasodilatation and a third early risk recognition phase ($p_3$) is provided.

The analysis may also take into account the absolute temperatures at measurement points 1 and 2, since zero gradient may occur due to massive drop in systemic blood pressure, or total occlusion of upper limb arterial circulation due to thrombus, thromboembolism or other physical cause, resulting in equalization of the temperature gradient due to temperature drop at the wrist (or distal antebrachium) level. Absolute values are also taken into account to detect zero gradient during hyperthermia or fever which may occur during warm shock due to sepsis. For example alcohol drinking and physical exercise may result in peripheral vasodilatation resulting in zero gradient while smoking may result in increased gradient, as an example.

According to an embodiment also a) heart rate and/or b) blood oxygen saturation of the patient are measured by a pulse oximeter so that the measurement signals are generated representing said heart rate and/or blood oxygen saturation. In the embodiment a fourth early risk recognition phase ($p_4$) is provided if a) the determined heart rate [like 50-100 hits/min in rest] and/or b) the blood oxygen saturation [like 90-100% in rest] based on said measurement signals is not in the predetermined range.

The peripheral vasoconstriction and peripheral cooling occurring due to multiple causes in hospitalized patients may cause pulse oximeter to overestimate the blood oxygen saturation. In contrast, hyperthermia may cause underestimation of the blood oxygen saturation. The condition caused by hypothermia may result in failure to detect life-threatening condition, i.e. overestimation of $SpO_2$. Thus there might be a need for ensuring the validity of the pulse oximeter readings.

According to an embodiment the measurement signals of the pulse oximeter may be validated by taking into account the temperature gradient ($\Delta t$) between said first and second points, and the absolute temperatures ($t_1$), ($t_2$) and ($t_3$), and if the temperature gradient ($\Delta t$) as well as also absolute temperatures ($t_1$), ($t_2$) and ($t_3$) are within their predetermined ranges, said reliability of the measurement signals are validated. If these values are out of predetermined ranges, the readings of the pulse oximeter are considered unreliable. An indication of reliability can be transmitted to the end device of the healthcare personnel, as well as to the wristband device worn by the patient.

The functional principle of the pulse oximeter is based on optical and noninvasive measurement of blood oxygen saturation and pulse. Peripheral vasoconstriction due to decrease of blood pressure or due to exposure to low or high ambient temperature will result in biasing of the pulse oximeter outputs, namely the heart rate and blood oxygen saturation. Skin temperature gradient and absolute readings in combination with ambient temperature measurement can be used to overcome these problems. In the present invention, the ambient temperature is measured using classical thermistor.

Also a respiratory rate of the patient may be determined based on for example baseline modulation, amplitude modulation and pulse period variations of the measurement signals generated by the pulse oximeter, and a fifth early risk recognition phase ($p_5$) provided if the respiratory rate is not in the predetermined range.

In addition also blood pressure of the patient may be determined. The determination is made advantageously in a non-invasive and continuous way and a sixth early risk recognition phase ($p_6$) is provided if said blood pressure is not in a predetermined range. The blood pressure can be monitored continuously for example with a technique called pulse transit time (PTT), defined as the transit time for a pressure pulse launched by a heartbeat in a patient's arterial system.

The measurement data of the patient is advantageously gathered by a wristband device and transferred to a (centralized) data processing unit via a two-way data communication link between said wristband device and data processing unit for the monitoring and early risk recognition determination processes. The wristband device advantageously comprises a first temperature sensor configured to measure first temperature ($t_1$) of the patient at the first wrist (or distal antebrachium) point, and a second temperature sensor configured to measure second temperature ($t_2$) of the patient at the second finger point. The first and second temperature sensors are for example infrared sensors, or the like. In addition the device comprises a wireless data communication means for communicating said measured data wirelessly to a data processing unit (so called backend).

The wristband device advantageously comprises also a third temperature sensor configured to measure ambient air temperature ($t_3$). The third temperature sensor is advantageously a thermistor located in the outer rim of the wristband. In addition the wristband device may further comprise at least one of the following: the pulse oximeter, photoplethysmogram (PPG) sensor, a locating means for locating said wristband device (such as a GPS means or means for localizing said device based on signals received from wireless base stations in the coverage area of said stations), a magnetometer in conjunction with an accelerometer, and a wireless data communication means for wirelessly receiving measurement controlling data from the data processing unit for controlling the measurement parameters of the device, like controlling a sensor to be read, sample frequency, inquiring power consumption or battery state of the device. For example in the normal state the wristband may have a first measuring frequency, but if the system determines some abnormal values, for example, it may send a control command to the wristband device to measure with a second measuring frequency being higher than said first measuring frequency. The system may also ask measuring values of another sensors, such as ambient temperature sensor, acceleration sensor, location sensor, or the like sensor which are normally not read, if the measured values indicates some abnormality (e.g $\Delta t$ is not within a predetermined limit). By this the energy-consumption can be minimized and very energy-efficient wristband device can be achieved.

The wristband device may also comprise an accelerometer (with or without gyroscopers and magnetometers) for determining accelerations of the user and communicating said acceleration data to the data processing unit. The system may thereby determine the movements of the user and send e.g. a trigger data to the wristband device to perform a predetermined act, if the movements of the user are not within predetermined values, for example if $\Delta t$ is not within a predetermined limit and the user has not moved in a certain time limit. The predetermined act may be e.g. an alarm, query, or sound or light indication or the like which need some feedback from the user, such as acknowledgement or pressing a button. If the system is not received any feedback from the user, if may perform an alarm to a healthcare personnel and send coordinates and other information of the user read and sent by the wristband device, for example.

The wristband device may also have indication means for indicating for example generated warning, such as sound, light, colour coded light, vibrating or messaging means or combination thereof.

In addition according to an embodiment a warning indication (such as a message, sound, colour coded light, vibration, noise, etc.) is sent to an end device of health care personnel when any early risk phase is recognised for the patient. The type of the warning indication may depend on the type/phase of the early risk recognition. Optionally also location information related to the location/position of the wristband device may be sent.

The invention offers remarkable advantages such as continuous and non-interfering measurement, which therefore allows also monitoring of pulse oxygen, because there is no any interruption in the blood circulation. In addition the invention provides an easy, hygienic and small in size mobile monitoring technology, because the monitoring can be implemented in minimum by using only few temperature sensors and with wireless data transmission and thus there is no need for a numbers of sensors connected to the device with long wires. Furthermore the monitoring system is reliable with low energy consumption. For example the reliability of the measurement of blood oxygen can be ensured by other measurements. In addition, the infrared measurement is rapid and capable of detecting transient alterations. Furthermore the measurement is insensitive to movement artefacts. It does not necessitate tight contact with the skin, which makes the measurement comfortable and reliable, and does not interfere possible other measurement devices or the blood circulation. Moreover when the second finger point locates at a root end of the finger, the fingertips are left free, which additionally makes the device more comfortable to the user.

The exemplary embodiments presented in this text are not to be interpreted to pose limitations to the applicability of the appended claims. The verb "to comprise" is used in this text as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific example embodiments when read in connection with the accompanying drawings.

BRIEF DESCRIPTION OF THE DRAWINGS

Next the invention will be described in greater detail with reference to exemplary embodiments in accordance with the accompanying drawings, in which.

DETAILED DESCRIPTION

Figure 1:
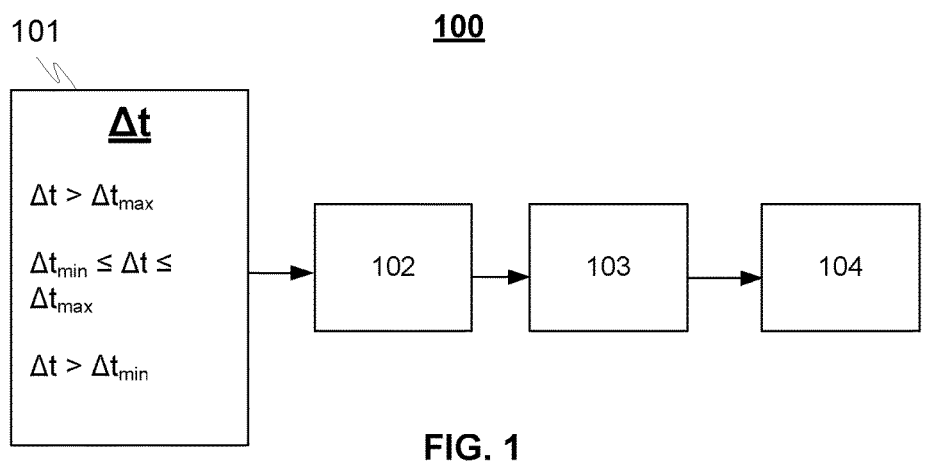
FIG. 1 illustrates a principle of an exemplary method for providing an early risk recognition monitoring according to an advantageous embodiment of the invention.

FIG. 1 illustrates a principle of an exemplary method 100 for providing an early risk recognition monitoring according to an advantageous embodiment of the invention, where the skin temperature gradient (Δt) between the first and second points (which are advantageously finger root and distal antebrachium at wrist area in this example) is determined. In addition also ambient temperature is measured in the example.

If the temperature gradient (Δt) exceeds the upper limit ($\Delta t_{max}$) of the predetermined range in step 101, the ambient temperature is determined in step 102. If the ambient temperature is low (so below a predetermined threshold) and additionally a) finger temperature is low, and b) wrist (or distal antebrachium) temperature in step 103 is normal; the state of the patient is construed in step 104 as decreased perfusion (peripheral vasoconstriction), but it is due to cold exposure (low ambient temperature). However, if the ambient temperature determined in step 102 is normal (within a predetermined temperature range) and additionally a) finger temperature is low, and b) wrist (or distal antebrachium) temperature is normal in step 103; the state of the patient is construed in step 104 as decreased perfusion (peripheral vasoconstriction), but it is due to moderate systemic pressure drop, like hemorrhagia, cardiogenic shock, cold phase of septic shock, peripheral arterial occlusion; and an early risk recognition phase is provided, correspondingly.

If the temperature gradient (Δt) is within the predetermined range in step 101, the state of the patient is construed in step 104 as normal perfusion.

This means that both the finger temperature and wrist (or distal antebrachium) temperature are normal and there is no need to measure them. It is to be noted that in this phase there is even no need to determine the ambient temperature, which can be whatever, and thus steps 102 and 103 can be skipped.

If the temperature gradient (Δt) deceeds the lower limit ($\Delta t_{min}$) of the predetermined range in step 101 (so Δt is below the range), the ambient temperature is determined in step 102. If the ambient temperature is high (so over a predetermined threshold) and additionally a) finger temperature is high, and also b) wrist (or distal antebrachium) temperature in step 103 is high the state of the patient is construed in step 104 as normal or hyperperfusion (peripheral vasoconstriction, but due to exposure to high ambient temperature). If the ambient temperature in step 102 is normal (so within a predetermined threshold) and additionally a) finger temperature and also b) wrist (or distal antebrachium) temperature in step 103 are high; the state of the patient is construed in step 104 as hyperperfusion (but due to warm phase of septic shock), and an early risk recognition phase is provided, correspondingly.

However, if the ambient temperature in step 102 is normal (so within a predetermined threshold) but both a) finger temperature and also b) wrist (or distal antebrachium) temperature in step 103 are low (so below a predetermined threshold); the state of the patient is construed in step 104 as decreased perfusion (total arterial occlusion due to physical arterial block (thrombosis, embolism, external cause) OR due to major systemic pressure drop (hemorrhagia, cardiogenic shock, cold phase of septic shock); and an early risk recognition phase is provided, correspondingly.

Figure 2A:
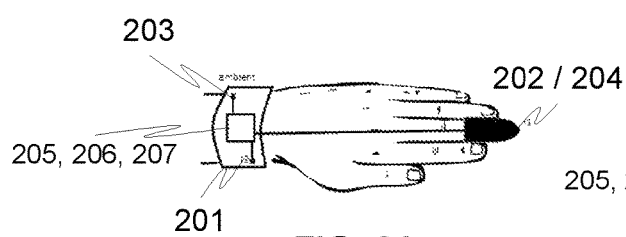
FIGS. 2A-C illustrate exemplary wristband devices for gathering measurement data of a patient in order to provide an early risk recognition according to an advantageous embodiment of the invention.
Figure 2B:
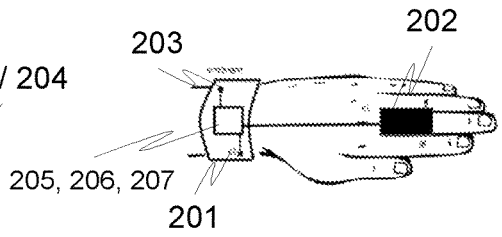
Figure 2C:
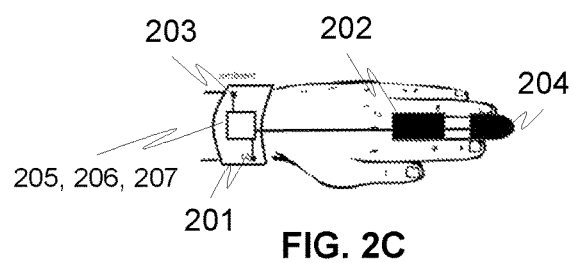

FIGS. 2A-C illustrate exemplary wristband devices 200 for gathering measurement data of a patient in order to provide an early risk recognition according to an advantageous embodiment of the invention. The wristband device 200 comprises advantageously a first temperature sensor 201 configured to measure first temperature ($t_1$) of the patient at the first wrist (or distal antebrachium) point, and a second temperature sensor 202 configured to measure second temperature ($t_2$) of the patient at the second finger point, advantageously at the finger root area. The first and second temperature sensors may be implemented e.g. by infrared sensors or thermistors.

In addition the wristband devices 200 may also comprise a third temperature sensor 203 configured to measure ambient air temperature ($t_3$) by a thermistor located in the outer rim of the wristband.

According to an embodiment the wristband devices 200 may also comprise a pulse oximeter 204, a locating means 205 for locating said wristband device (such as a GPS means or means for localizing said device based on signals received from wireless base stations in the coverage area of said stations), as well as wireless data transferring means 206 (for both sending measurement data to data processing unit and receiving measurement controlling data from the data processing unit for controlling the measurement parameters of the device, as an example). According to an example also an accelerometer 207 may be comprised. The accelerometer may be e.g. 3D MEMS accelerometer (with or without gyroscopes or magnetometers) or the like.

Figure 3:
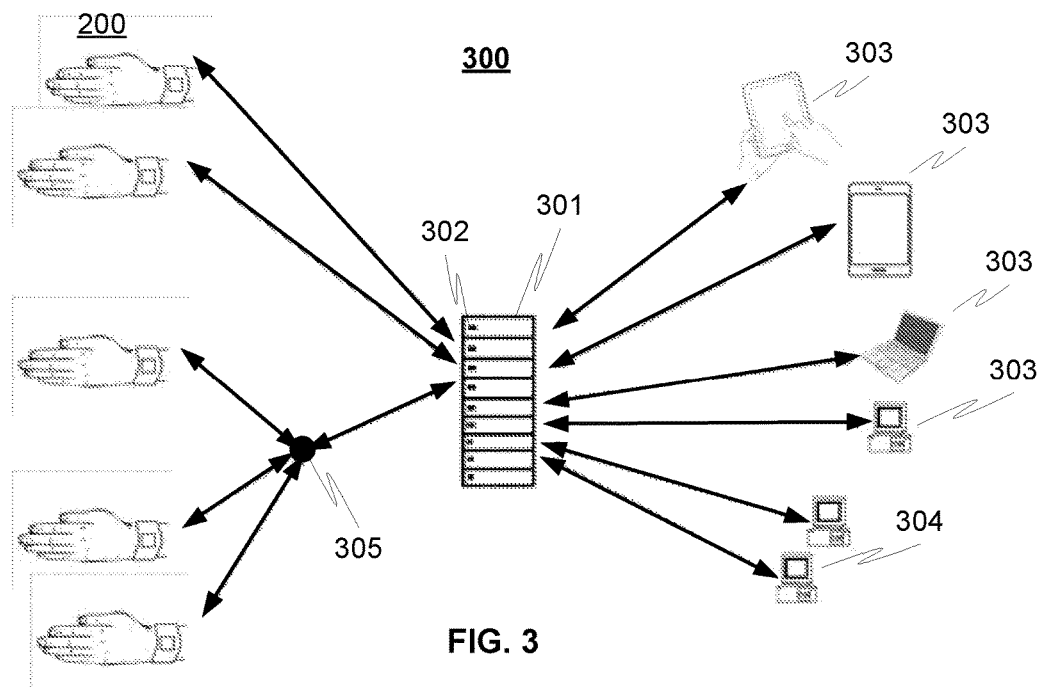
FIG. 3 illustrates a principle of an exemplary system for providing an early risk recognition monitoring according to an advantageous embodiment of the invention.

FIG. 3 illustrates a principle of an exemplary system 300 for providing an early risk recognition monitoring according to an advantageous embodiment of the invention, where the system comprises a first temperature sensor 201 for measuring first temperature ($t_1$) of the patient at the first wrist point (or distal antebrachium), and a second temperature sensor for measuring second temperature ($t_2$) of the patient at the second finger point (location at fingertip, as an example). Advantageously the sensors are implemented by the wristband device 200, which transfers the measurement data to the data processing means 301 of the system.

The system 300 is configured to determine altered peripheral tissue perfusion (due to either peripheral vasoconstriction or vasodilatation or altered blood flow or combination) by determining the skin temperature gradient (Δt) by using the measured temperatures of ($t_1$) and ($t_2$) between said first and second points (like distal antebrachium-finger), and if the determined temperature gradient (Δt) exceeds a predetermined range [e.g. 1-4° C., most preferably 2-3° C.], the system is configured to construe:

an (Δt) exceeding of the upper limit of the range as said peripheral vasoconstriction or an (Δt) deceeding of the lower limit of the range as said peripheral vasodilatation, and thereby configured to provide first early risk recognition phase ($p_1$).

Advantageously the data processing unit 301 is configured to perform the analysis and thereby provide said early risk recognition phases described in this document. The data processing unit 301 advantageously algorithm analyses 302 the data received from the wristband device and possibly also extracts more bio-signals and based on the analysis alarms the medical staff if needed, so transmits warning indication of the early risk recognition phase to the end devices 303 of health care personnel when any early risk phase is recognised for the patient. The type of the warning indication may depend on the type/phase of the early risk recognition. The warning indication may be for example a message, sound, light, colour coded light, vibration, noise, or the like. Optionally also location information related to the location/position of the wristband device is sent from the wristband device to the data processing unit and again to the end devices 303 of health care personnel.

The system may also comprise a third temperature sensor configured to measure ambient air temperature ($t_3$) by a thermistor located in the outer rim of the wristband, a pulse oximeter, and a locating means for locating said wristband device. In addition the data processing unit 301 may be configured to send controlling data to the wristband device for controlling the measurement parameters of the device, such as managing the sensor to be read, sample frequency, inquiring power consumption or battery state, as an example, or triggering a warning indication at the wristband device.

The communication between the wristband device and backend system is advantageously two-way. Wristband device transmits measurement data to the backend application and depending on the outcome of the analysis, the backend application may provide feedback control to the wristband, for example regulation of the sampling rate. For example, the sampling rate may be decreased in healthy patients and increased in patients at high risk to optimize the power consumption of the wristband.

In addition the system 300 may also comprise additional data transferring means, such as workstation 304 for ward nurses and doctors for receiving the warnings or alarms from the data processing unit, as well as also for managing and operating the data processing unit, or even the operation of the wristband devices via said data processing unit. In addition the system may comprise hotspots 305 to enable better communication between the wristband devices 200 and the data processing unit 301 e.g. with different wireless protocol and to enable user, or wristband device location, as an example.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims. For example it is to be noted that even if the sensors, especially temperature sensor 202 and pulse oximeter are described in the same finger in Figures, they may also be located at different fingers with each other.

The invention claimed is:

1. A system for providing an early risk recognition monitoring by measurement of a peripheral tissue perfusion of a patient, wherein the system comprises:
    a wristband device for gathering measurement data of the patient; and
    a data processing unit for processing said measurement data in order to provide said early risk recognition monitoring, wherein said wristband device and data processing unit are configured to communicated with each other via a two-way data communication link so that said wristband device is configured to send said measurement data to the data processing unit for the monitoring and early risk recognition determination processes,
    wherein the wristband device comprises:
    a first infrared temperature sensor configured to measure a first temperature of the patient at a first wrist point, said first wrist point being at an area of distal antebrachium, and
    a second infrared temperature sensor configured to measure a second temperature of the patient at a second finger point, said second finger point being a root end of a finger,
    whereupon the data processing unit is configured to determine altered peripheral tissue perfusion by determining a temperature gradient between said first and second points, and if the determined temperature gradient exceeds a predetermined range, the data processing unit is configured to construe:
    the temperature gradient exceeding of the upper limit of the range as a peripheral vasoconstriction or
    the temperature gradient below the lower limit of the range as a peripheral vasodilatation,
    and thereby configured to provide first early risk recognition phase,
    wherein the measurement of the peripheral tissue perfusion is performed without interfering with blood circulation.

2. A system of claim 1, wherein the wristband device further comprises a third temperature sensor configured to measure a third ambient temperature at the third outer rim area of the patient's wrist being essentially at the area of distal antebrachium, whereupon, if the temperature gradient is exceeding, the data processing unit is configured to determine said third ambient temperature, and if the third ambient temperature is within a predetermined range, the data processing unit is configured to provide a second early risk recognition phase.

3. A system of claim 1, wherein the data processing unit is configured to determine absolute temperatures of the first and second temperatures in the case, where the temperature gradient is below a predetermined threshold and if the absolute temperatures of the first and second temperatures are within a predetermined range, the data processing unit is configured to construe the case as said peripheral vasodilatation and to provide a third early risk recognition.

4. A system of claim 1, wherein the system comprises also a pulse oximeter configured to measure a heart rate and a blood oxygen saturation of the patient and generate measurement signals representing said heart rate and blood oxygen saturation, and wherein the data processing unit is configured to provide a fourth early risk recognition phase if the heart rate or the blood oxygen saturation based on said measurement signals is not in a second predetermined range.

5. A system of claim 4,
    wherein the wristband device further comprises a third temperature sensor configured to measure a third ambient temperature,
    wherein the data processing unit is configured to validate the reliability of the measurement signals of the pulse oximeter by taking into account the temperature gradient between said first and second points, and the absolute temperatures of the first, second and third temperatures, and if the temperature gradient as well as also absolute temperatures of the first, second and third temperatures are within their predetermined ranges, the data processing system is configured to validate said reliability of the measurement signals.

6. A system of claim 4, wherein the data processing unit is configured to determine a respiratory rate of the patient based on baseline modulation, amplitude modulation or pulse period variations of the measurement signals generated by the pulse oximeter, and configured to provide a fifth early risk recognition phase if the respiratory rate is not in the predetermined range.

7. A system of claim 1, wherein the wristband device comprises an accelerometer with or without gyroscopes or magnetometers for determining accelerations of the user, and wherein the wristband device is configured to communicate acceleration data to the data processing unit, whereupon the data processing unit is configured to thereby determine the movements of the user and send a trigger data to the wristband device to perform predetermined act, if the movements of the user is not within predetermined values, wherein the predetermined act comprises an alarm, query, or sound or light indication.

8. A system of claim 1, wherein the wristband device comprises additionally:
a third temperature sensor configured to measure ambient air temperature by a thermistor located in the outer rim of the wristband,
a pulse oximeter, or
a locating device for locating said wristband device;
and wherein the data processing unit is configured to send controlling data to the wristband device for controlling the measurement parameters of the device or triggering a warning indication.

9. A system of claim 1, wherein the data processing unit is configured to send a warning indication to an end device of health care personnel when any early risk phase is recognized for the patient.

10. A method for providing an early risk recognition monitoring by measurement of a peripheral tissue perfusion of a patient, wherein the method comprises:
measuring a first temperature of the patient at a first wrist point with an infrared sensor, said first wrist point being at an area of distal antebrachium;
measuring a second temperature of the patient at a second finger point with an infrared sensor, said second finger point being a root end of a finger; and
determining altered peripheral tissue perfusion by determining a temperature gradient between said first and second points, and if the determined temperature gradient exceeds a predetermined range, construing:
the temperature gradient exceeding of the upper limit of the range as a peripheral vasoconstriction or
the temperature gradient below the lower limit of the range as a peripheral vasodilatation,
wherein the measurement of the peripheral tissue perfusion is performed without interfering with blood circulation.

11. A method of claim 10, further comprising determining a third ambient temperature in the case of the temperature gradient exceeding, where said measurement is done with a thermistor.

12. A method of claim 10, further comprising:
determining absolute temperatures of the first and second temperatures in the case where the temperature gradient is below a predetermined threshold, and
if the absolute temperatures of the first and second temperatures are within a predetermined range, construing the case as said peripheral vasodilatation.

13. A method of claim 10, further comprising:
determining a third ambient temperature with a temperature sensor,
measuring a heart rate and a blood oxygen saturation of the patient by a pulse oximeter and generating measurement signals representing said heart rate and blood oxygen saturation, and
validating the reliability of the measurement signals of the pulse oximeter by taking into account the temperature gradient between said first and second points, and the absolute temperatures of the first, second and third temperatures, wherein if the temperature gradient and the absolute temperatures of the first, second and third temperatures are within their predetermined ranges, said reliability of the measurement signals are validated.

14. A method of claim 13, further comprising determining a respiratory rate of the patient based on baseline modulation, amplitude modulation or pulse period variations of the measurement signals generated by the pulse oximeter.

15. A method of claim 10, further comprising gathering the measurement data of the patient by a wristband device and transferring the gathered measurement data to a data processing unit via a two-way data communication link between said wristband device and data processing unit for the monitoring processes.

16. A method of claim 15, further comprising transferring controlling data from the data processing unit to the wristband device for controlling the measurement parameters of the wristband device or triggering a warning indication in the wristband device.

17. A method of claim 10, further comprising sending a warning indication to an end device of health care personnel when any early risk phase is recognized for the patient.

18. A non-transitory computer-readable medium storing computer executable code, which when executed by a data processing unit, performs a method of providing an early risk recognition monitoring by measurement of a peripheral tissue perfusion of a patient, wherein the method comprises:
analyse a first temperature of the patient measured at a first wrist point with a first infrared temperature sensor, said first wrist point being at an area of distal antebrachium and
analyse a second temperature of the patient measured at a second finger point with a first infrared temperature sensor, said second finger point being a root end of a finger,
determine altered peripheral tissue perfusion by determining a temperature gradient between said first and second points, and if the determined temperature gradient exceeds a predetermined range, construe:
the temperature gradient exceeding of the upper limit of the range as a peripheral vasoconstriction or
the temperature gradient below the lower limit of the range as a peripheral vasodilatation,
and thereby provide a first early risk recognition phase
wherein the measurement of the peripheral tissue perfusion is performed without interfering with blood circulation.

* * * * *